United States Patent
Wong et al.

(10) Patent No.: US 11,471,514 B1
(45) Date of Patent: *Oct. 18, 2022

(54) DUAL-ENZYME COMPOSITION FOR PREVENTING, TREATING AND/OR ALLEVIATING VEISALGIA AND SYMPTOMS ASSOCIATED THEREWITH

(71) Applicant: ALCOLEAR LIMITED, Hong Kong (HK)

(72) Inventors: Bing Lou Wong, Irvine, CA (US); Sek Lun Law, Hong Kong (HK)

(73) Assignee: ALCOLEAR LIMITED, Hong Kong (HK)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,046

(22) Filed: Dec. 21, 2021

Related U.S. Application Data

(63) Continuation-in-part of application No. 17/308,995, filed on May 5, 2021, now Pat. No. 11,208,631.

(51) Int. Cl.
*A61K 38/44* (2006.01)
*C12N 9/02* (2006.01)
*C12N 9/04* (2006.01)

(52) U.S. Cl.
CPC .......... *A61K 38/443* (2013.01); *C12N 9/0006* (2013.01); *C12N 9/0008* (2013.01); *C12Y 101/01001* (2013.01); *C12Y 102/01003* (2013.01)

(58) Field of Classification Search
None
See application file for complete search history.

(56) References Cited

U.S. PATENT DOCUMENTS

2005/0271739 A1 12/2005 Wang
2005/0271754 A1 12/2005 Cochrane

FOREIGN PATENT DOCUMENTS

| CN | 109718255 A | 5/2019 |
| CN | 114377113 A | 4/2022 |
| WO | 2005049002 A1 | 6/2005 |

OTHER PUBLICATIONS

Buddy T, "Alcohol Metabolism Could Be Key to Risks of Drinking," https://www.verywellmind.com/alcohol-metabolism-key-to-alcohols-dangers-66524, 2020, pp. 1-14.
International Search Report and Written Opinion of the corresponding PCT application No. PCT/CN2022/090852 dated Aug. 4, 2022.

*Primary Examiner* — Kagnew H Gebreyesus
(74) *Attorney, Agent, or Firm* — Idea Intellectual Limited; Margaret A. Burke; Sam T. Yip

(57) ABSTRACT

A composition includes two exogenous enzymes from animals for consumption by human beings to prevent, treat and/or alleviate veisalgia and/or symptoms associated therewith arising from or caused by consumption or spontaneous production of alcohol through a dual-enzyme based breakdown of the alcohol, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and $NAD^+/NADH$, and wherein the first enzyme to the second enzyme is in a molar ratio of 1:3-51 in the composition in order to avoid an elevation in the level of the first metabolite in the human being.

13 Claims, 13 Drawing Sheets

Specification includes a Sequence Listing.

DUAL-ENZYME COMPOSITION FOR PREVENTING, TREATING AND/OR ALLEVIATING VEISALGIA AND SYMPTOMS ASSOCIATED THEREWITH

CROSS-REFERENCE TO RELATED APPLICATIONS

This application is a continuation-in-part of the U.S. non-provisional patent application Ser. No. 17/308,995 filed May 5, 2021 and issued under the U.S. Pat. No. 11,208,631 on Dec. 28, 2021, and the disclosure of which is incorporated herein by reference in its entirety.

FIELD OF THE INVENTION

The present invention relates to a dual-enzyme composition for preventing, treating and/or alleviating veisalgia and symptoms associated therewith, and, more particularly, to assisted enzyme-based breakdown of alcohol within the human body.

BACKGROUND

The effect of ingested beverage alcohol (ethanol) on different organs in human body, including the brain/Central Nervous System, liver & pancreas, depends on the ethanol concentration intake and the duration of exposure. Both of these variables are affected by the absorption of ethanol into the blood stream and tissues as well as by ethanol metabolism[5]. The primary enzymes in the human body involved in ethanol metabolism are Alcohol Dehydrogenase ("ADH") and Aldehyde Dehydrogenase ("ALDH"). The main pathway of ethanol metabolism involves its oxidation to acetaldehyde, a reaction that is catalysed by ADH and co-enzyme NAD+. In a second reaction catalyzed by ALDH and co-enzyme NAD+, acetaldehyde is oxidized to acetic acid. This metabolism is illustrated as FIG. 1. The mechanism through which ADH and ALDH influences alcoholism risk is thought to involve local elevation of acetaldehyde levels, resulting either from a more rapid ethanol oxidation or from a slower acetaldehyde oxidation. Acetaldehyde is a toxic substance whose accumulation leads to highly adverse reactions that include facial flushing, nausea, rapid heart rate and veisalgia, and symptoms associated therewith (FIG. 1).

Recently, many people use over-the-counter pain relievers, like aspirin or acetaminophen, to relieve veisalgia and symptoms associated therewith. It is important to recognize that the combination of alcohol and acetaminophen can be toxic to the liver. Furthermore, there is no medication for acute alcohol intoxication. Haemodialysis is the only option in emergency cases, especially in the US, where the medicine Metadoxin has not been approved by the FDA. Consequently, the development of innovative preventive measures which can effectively minimize the risk of potential health hazards brought about by drinking alcohol has become a very important strategy to lessen the burden on the overall economy. There is a huge void in the healthcare market for a product which is effective, safe and convenient for daily use as a prophylaxis measure for casual and frequent alcohol drinkers and patients suffering from alcohol use disorder.

As seen from the various alcohol ingestion-related problems, there is a need in the art to enhance the breakdown of alcohol in the human body. Enhanced breakdown of alcohol and alcohol metabolism products would reduce long-term harmful effects from alcohol such as liver damage, and short-term effects such as veisalgia and alcohol poisoning. Thus, there is a need in the art for compositions that can enhance the breakdown of alcohol in the human body that are low-cost and have minimal side effects.

In addition, certain populations may experience spontaneous production of alcohol in the gut, leading to a common condition known as Non-Alcoholic Fatty Liver Disease ("NAFLD"). A composition that would metabolize such spontaneously accumulated alcohol would relieve the suffering of large numbers of persons with this ailment.

SUMMARY OF THE INVENTION

In one aspect, there is provided a composition including two exogenous enzymes from animals for consumption by human beings before and/or after consuming alcohol to prevent, treat and/or alleviate veisalgia and/or symptoms associated therewith arising from or caused by consumption of alcohol or production of alcohol in the body in patients with NAFLD, wherein a first enzyme of the two exogenous enzymes is capable of converting alcohol into a first metabolite while a second enzyme thereof is capable of converting the first metabolite into a second metabolite which is excretable to systemic circulation after an oxidation reaction of the alcohol in the presence of the two exogenous enzymes and NAD+/NADH, and wherein the first enzyme to the second enzyme is in a molar ratio of 1:3-51 in the composition in order to avoid local elevation of the first metabolite in the human being after consumption of alcohol.

In one embodiment, the first enzyme is alcohol dehydrogenase and the second enzyme is aldehyde dehydrogenase.

In another embodiment, the first enzyme to the second enzyme in the composition is in a molar ratio in the range of approximately 1:3 to approximately 1:51 (while our experiments have been conducted only up to a ratio of 1:51, variations in the sourced bovine liver material may increase the ratio by as much as 10% to 1:56).

In other embodiment, the local elevation of the first metabolite leads to veisalgia symptoms.

In yet another embodiment, the first metabolite is acetaldehyde.

In other embodiment, the second metabolite is acetate.

In also another embodiment, the symptoms associated with veisalgia comprise fatigue, apathy, concentration problems, clumsiness, confusion, thirst, sweating, shivering, stomach pain, nausea, dizziness and heart pounding.

In an embodiment, the aldehyde dehydrogenase is represented by an amino acid sequence of SEQ ID NO: 1.

In an embodiment, the animals from which the two exogenous enzymes are comprise bovine, ovine, equine and galline.

In other embodiment, the exogenous enzymes are from livers of bovine, ovine, equine and galline.

The at least two different exogeneous enzymes can be sourced from the same or two different origins of animal.

More specifically, the at least two different exogeneous enzymes are sourced from the same original of animal, and the animal is selected from bovine, ovine, equine, or galline.

Alternatively, the at least two different exogeneous enzymes are sourced from different origins of animal, and the animal is selected from bovine, ovine, equine, galline, anas, or any combination thereof.

The at least two different exogeneous enzymes are more abundant in livers than other body parts of the animal.

In certain exemplary embodiments, the composition of the present invention is consumed orally by the subject before and/or after the alcohol consumption.

The at least two different exogenous enzymes can be in solid form.

The composition can also be formulated into a controlled-release system, and further include an enteric coating encapsulating the at least two different exogenous enzymes to form an enteric capsule, tablet and/or pill.

Another aspect of the present invention provides a method for lowering alcohol content and/or preventing accumulation of one of metabolites of the alcohol causing veisalgia and symptoms associated therewith in a subject, including consuming the composition of the present invention by the subject before and/or after consuming alcohol.

As described hereinabove, the composition can be formulated in an enteric capsule, tablet, and/or pill which enables a controlled-release system of delivering the at least two different exogenous enzymes to a target site of the subject.

The at least two different exogenous enzymes are delivered to blood streams via gastrointestinal tract of the subject.

As described hereinabove, the at least two different exogeneous enzymes can be in solid form.

There is provided at least 89% of a population of the same subject is absent of veisalgia and symptoms associated therewith after consuming an effective amount of the composition prior to or after consumption of alcohol.

DEFINITIONS

Figure 1:
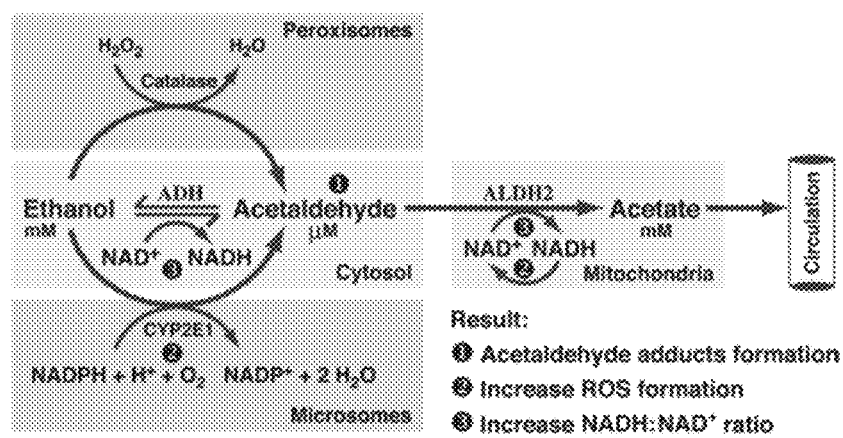
FIG. 1 schematically illustrates the general mechanism of how ADH and ALDH2 metabolize alcohol in a human body.
Figure 2:
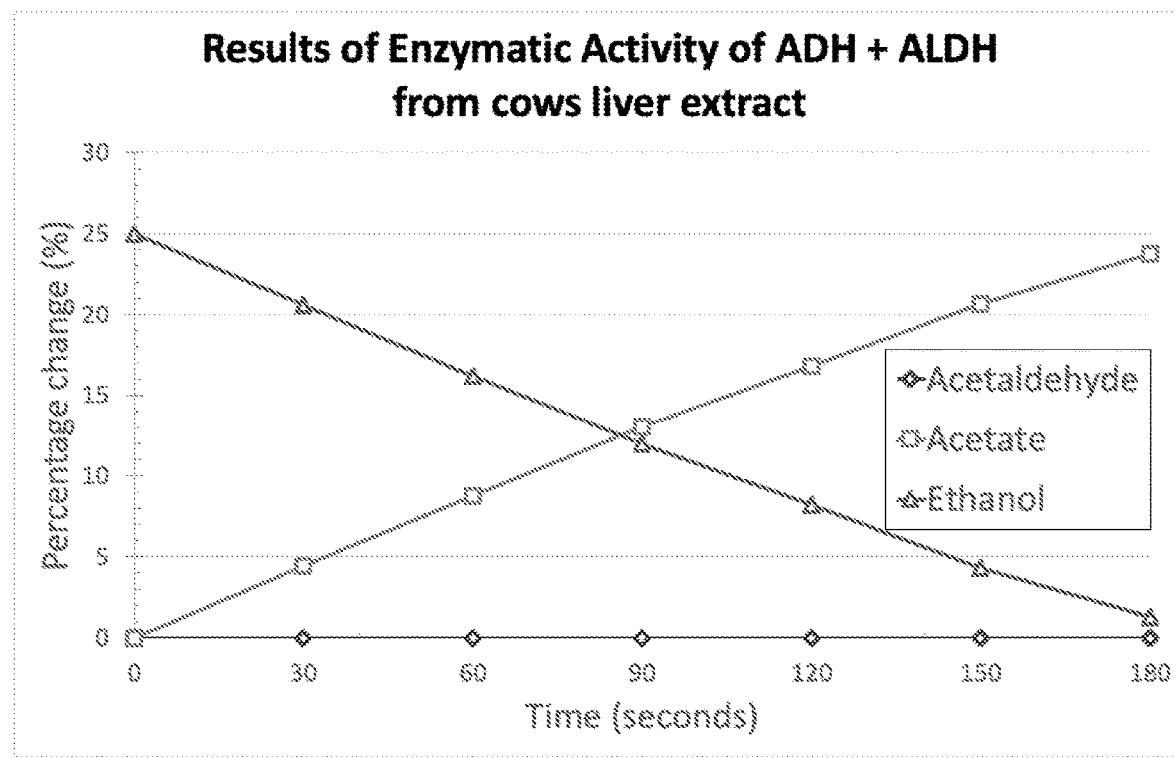
FIG. 2 shows the result of in vitro enzymatic activity of the present composition from extract of cows' liver in terms of the change in concentration of alcohol and its by-products or metabolites over time.
Figure 3:
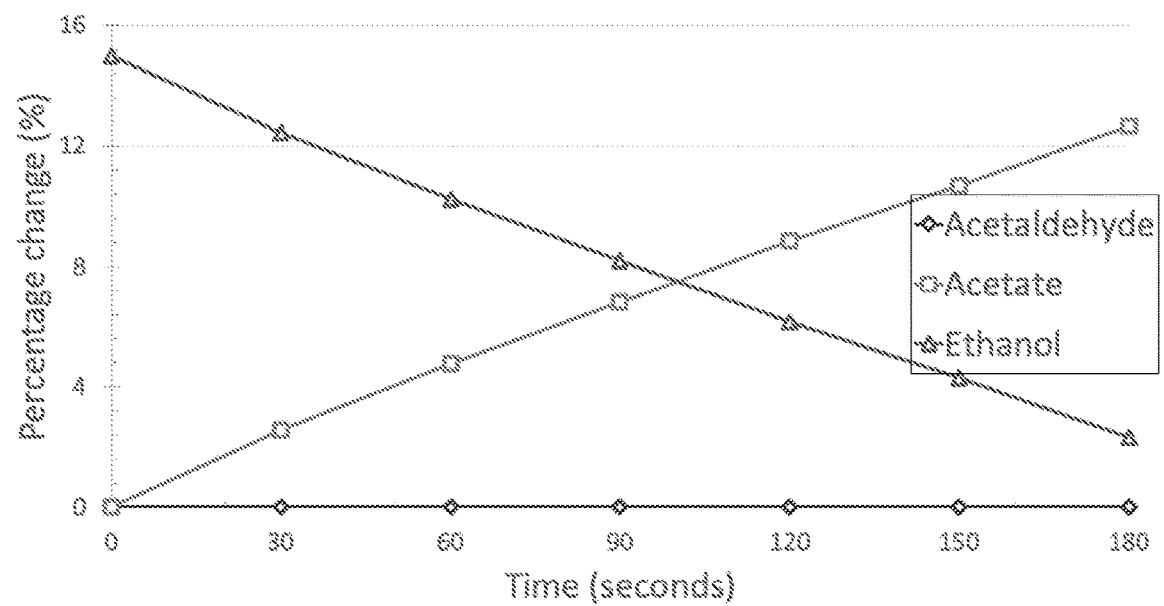
FIG. 3 shows the result of in vitro enzymatic activity of the present composition from extract of lambs' liver in terms of the change in concentration of alcohol and its by-products or metabolites over time.
Figure 4:
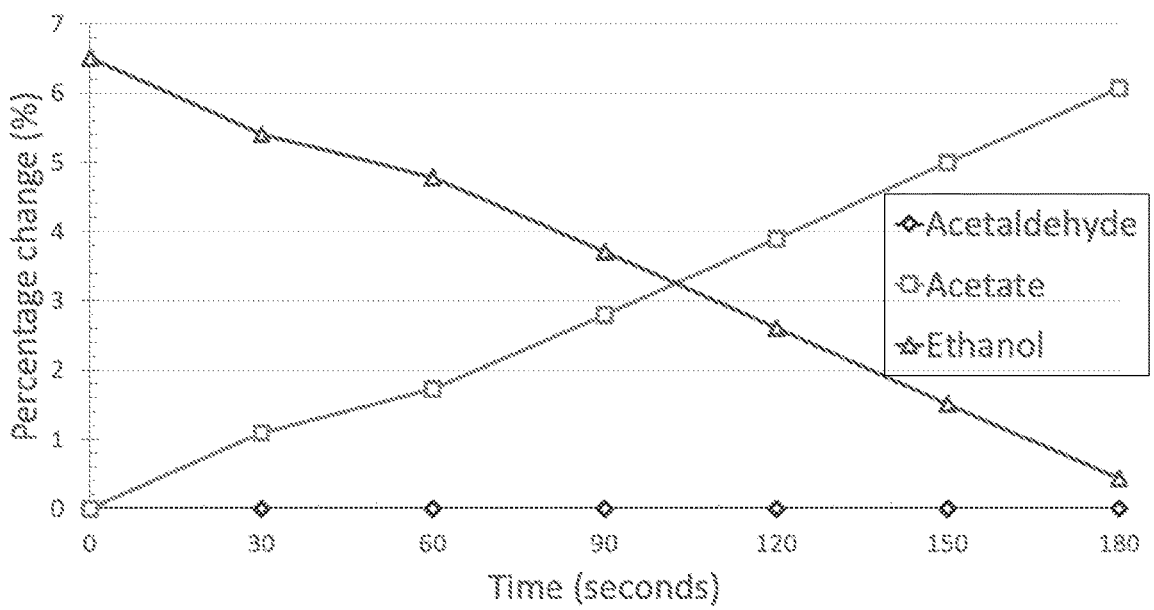
FIG. 4 shows the result of in vitro enzymatic activity of the present composition from extract of sheep' liver in terms of the change in concentration of alcohol and its by-products or metabolites over time.
Figure 5:
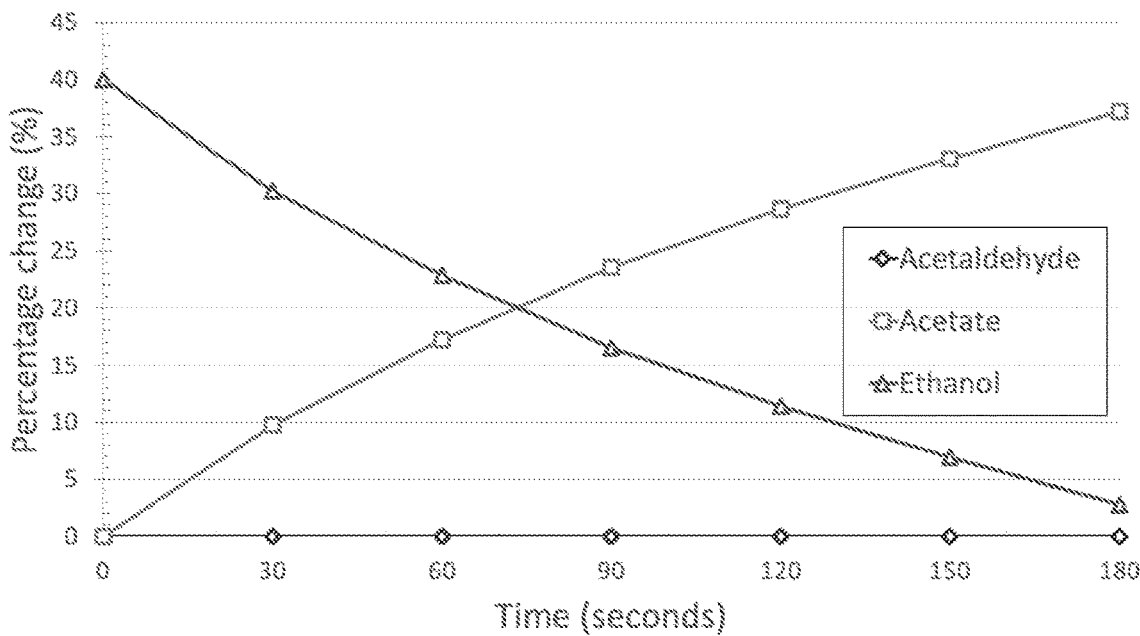
FIG. 5 shows the result of in vitro enzymatic activity of the present composition from extract of horse liver in terms of the change in concentration of alcohol and its by-products or metabolites over time.
Figure 6:
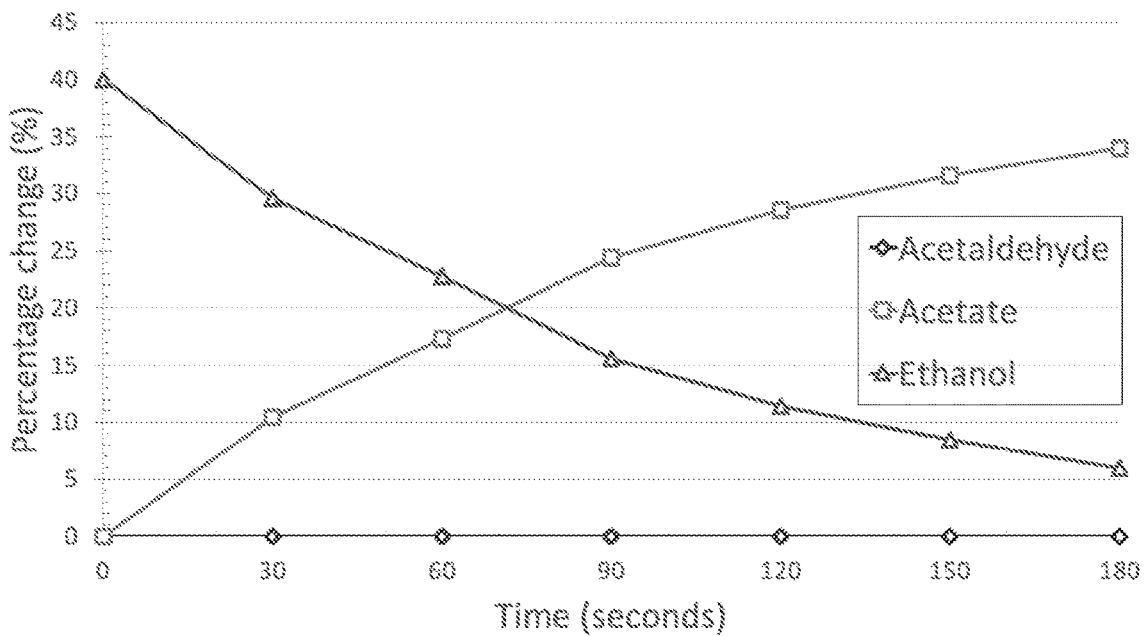
FIG. 6 shows the result of in vitro enzymatic activity of the present composition from extract of donkey liver in terms of the change in concentration of alcohol and its by-products or metabolites over time.
Figure 7:
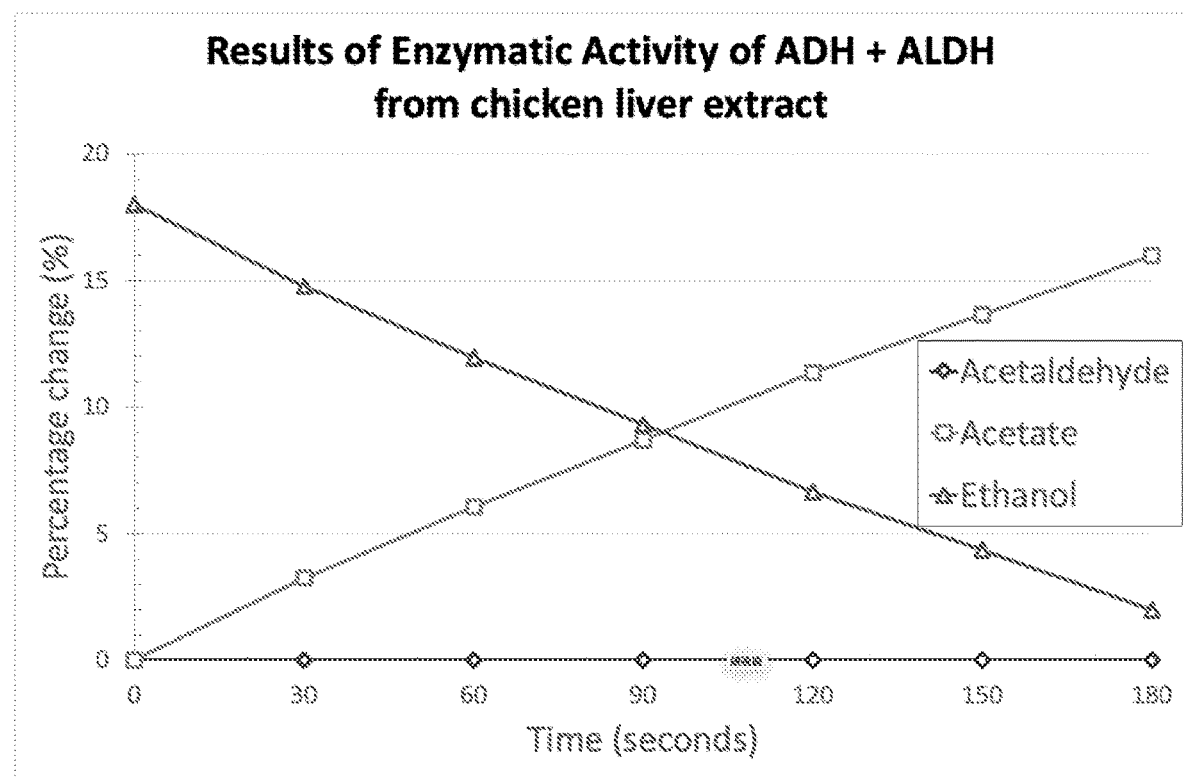
FIG. 7 shows the result of in vitro enzymatic activity of the present composition from extract of chicken liver in terms of the change in concentration of alcohol and its by-products or metabolites over time.

The following abbreviations and their corresponding long expressions are used herein interchangeably:
ADH—Alcohol Dehydrogenase
AHSS—Alcohol Hangover Severity Scale
ALDH—Aldehyde Dehydrogenase
AUD—Alcohol Use Disorder
FDA—Food and Drug Administration
I.M.—intramuscular
I.V.—intravenous
NAFLD—non-alcoholic fatty liver disease
US—United States
WHO—World Health Organization Throughout the present application, any numerical value or range presented with the term "about', "approximately", or alike, is understood by a skilled artisan to refer to also include those values near a recited value or near the upper and lower limits of a recited range. For example, "about 40 [units]" may mean within ±25% of 40 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Also, the terms "about" and "approximately" are used herein interchangeably throughout the present application.

Further, the term "approximately" is to cover minor variations to the composition that do not affect the activity of the overall composition. That is, minor changes that produce the same effects as the claimed composition are intended to be included in the scope of the appended claims.

For numerical ranges provided for certain quantities, it should be understood that these ranges also cover subranges therein. For example, the range "from 50 to 80" includes all possible ranges therein (e.g., 51-79, 52-78, 53-77, 54-76, 55-75, 70-70, etc.).

Furthermore, all values within a given range may be an endpoint for the range encompassed thereby (e.g., the range 50-80 includes the ranges with endpoints such as 55-80, 50-75, etc.).

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR, Raman spectroscopy or XRPD; and to indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately".

Further, it is understood that, when active ingredient ranges are applied to human populations, there is a wide range of body weights that receive approximately the same dosage. Therefore, the amount of active ingredient per kg of body weight has a natural range when a dose of, for example, 100 mg is applied to patients with weights ranging from 50 kg to over 100 kg. Therefore, the experimental results shown in the present disclosure can naturally be extrapolated over the ranges described as "approximate" and "about" as set forth above.

DETAILED DESCRIPTION

1. Mechanism of the Present Invention:

Enzymes are macromolecular biological catalysts, which can accelerate chemical reactions in the human body. Almost all metabolic processes in cells need enzyme catalysis in order to occur at rates fast enough to sustain life. Enzymes are known to catalyse more than 5,000 biochemical reactions. Most enzymes are proteins, and the specificity comes from their unique three-dimensional structures. As many enzymes are naturally produced by the human body, they are safe to use as supplements that may be ingested.

The present invention focuses on two enzymes for alcohol metabolism, namely Alcohol Dehydrogenase ("ADH") and Aldehyde Dehydrogenase ("ALDH"). ADH is an enzyme found primarily in the liver and stomach that converts ethanol to acetaldehyde, a toxin which is then further broken down by ALDH to acetate, which can be converted to carbon dioxide and water. These two enzymes were studied using in vitro assays, proving that the corresponding enzymatic activity is highly potent, and could potentially be used to enhance the degradation of alcohol in the human body for alcohol drinkers to prevent as well as treat and/or alleviate veisalgia and symptoms associated therewith. These enzymes may also be used to treat those whose faulty microbiomes are overproducing ethanol from non-alcohol-based food and beverages leading to non-alcoholic fatty liver disease ("NAFLD"). Thus, the compositions may be effective in reducing or preventing NAFLD.

In one aspect, ADH and ALDH were tested, in vitro, to determine activity on ethanol substrates. The ADH and ALDH were sourced from mammal or ayes livers, a plentiful natural source for the starting material that can contribute to production of a low-cost oral supplement.

The enzymes tested use a molar ratio of ADH and ALDH ranging from approximately 1:3 to approximately 1:51, to enable the second step of the enzymatic alcohol degradation process to be the dominant enzymatic reaction. The rationale for developing such a formulation is to prevent the accumulation of acetaldehyde, which is the major cause of veisalgia and symptoms associated therewith. Using this formulation, acetaldehyde, the breakdown product from alcohol in the first step of enzymatic process, is effectively degraded to acetic acid and eventually water and carbon dioxide.

2. Formulations Used in the Present Invention

The ADH and ALDH from the livers of nine animals including cow, lamb, sheep, pig, horse, donkey, chicken, duck and goose were tested, in vitro, to determine activity on alcohol and aldehyde substrates in order to find out the molar ratio of ADH:ALDH from their liver extract. Pig, duck and goose livers were found not to contain ALDH.

Example 1—Cows (Bovine)

The cow liver is sourced from Australia in frozen form. The in vitro enzymatic activity results from liver of cows (from dry powder of cows' liver extract when the concentration is about 50 mg/ml) for ADH is on average 3.25 Unit and for ALDH is on average 91.31 Unit. The molar ratio of ADH:ALDH is rounded up to 1:28.

Example 2—Lamb (Ovine)

The lamb liver is sourced from Australia in frozen form. The in vitro enzymatic activity results from liver of lamb (from dry powder of lamb liver extract when concentration is about 50 mg/ml) for ADH is on average 1.60 Unit and for ALDH is on average 63.09 Unit. The molar ratio of ADH:ALDH is rounded up to 1:39.

Example 3—Sheep (Ovine)

The sheep liver is sourced from Australia in frozen form. The in vitro enzymatic activity results from the livers of sheep (from dry powder of sheep liver extract when concentration is about 50 mg/ml) for ADH is on average 0.80 Unit and for ALDH is on average 40.65 Unit. The molar ratio of ADH:ALDH is rounded up to 1:51.

Example 4—Pig (Swine)

Figure 9:
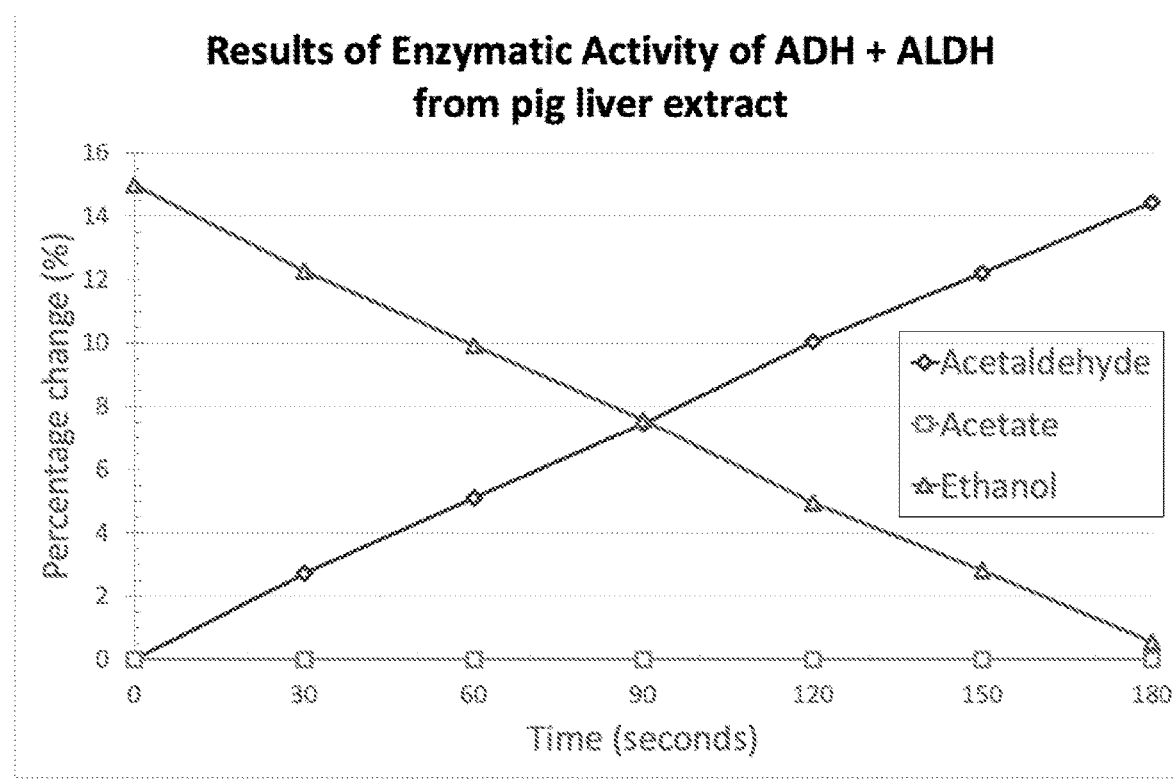
FIG. 9 shows the result of in vitro enzymatic activity from an extract of pig liver in terms of the change in concentration of alcohol and its by-products or metabolites over time showing no increase in acetate due to the liver not containing ALDH.

The pig liver is sourced from local markets in Hong Kong and is fresh. Pig liver was determined to only have the ADH enzyme without the ALDH enzyme. The in vitro enzymatic activity results from the liver of pigs (from dry powder of pig liver extract when concentration is about 50 mg/ml) for ADH is 3.51 Unit. As seen in FIG. 9, there is no increase in acetate due to the liver not containing ALDH.

Example 5—Horse (Equine)

The horse liver is sourced from China in frozen form. The in vitro enzymatic activity results from the livers of horses (from supernatant of crude extract of horse liver) for ADH is 9.04 Unit and for ALDH is 42.67 Unit. The molar ratio of ADH:ALDH is rounded up to 1:5.

Example 6—Donkey (Equine)

The donkey liver is sourced from China in fresh form. The in vitro enzymatic activity results from livers of donkeys (from supernatant of crude extract of donkey liver) for ADH is 9.87 Unit and for ALDH is 184.00 Unit. The molar ratio of ADH:ALDH is rounded up to 1:19.

Example 7—Chicken (Galline)

The chicken liver is sourced from local markets in Hong Kong in fresh form. The in vitro enzymatic activity results from livers of chickens (from supernatant of crude extract of chicken liver) for ADH is 2.96 Unit and for ALDH is 8.09 Unit. The molar ratio of ADH:ALDH is rounded up to 1:3.

Example 8—Duck (Anas)

Figure 8:
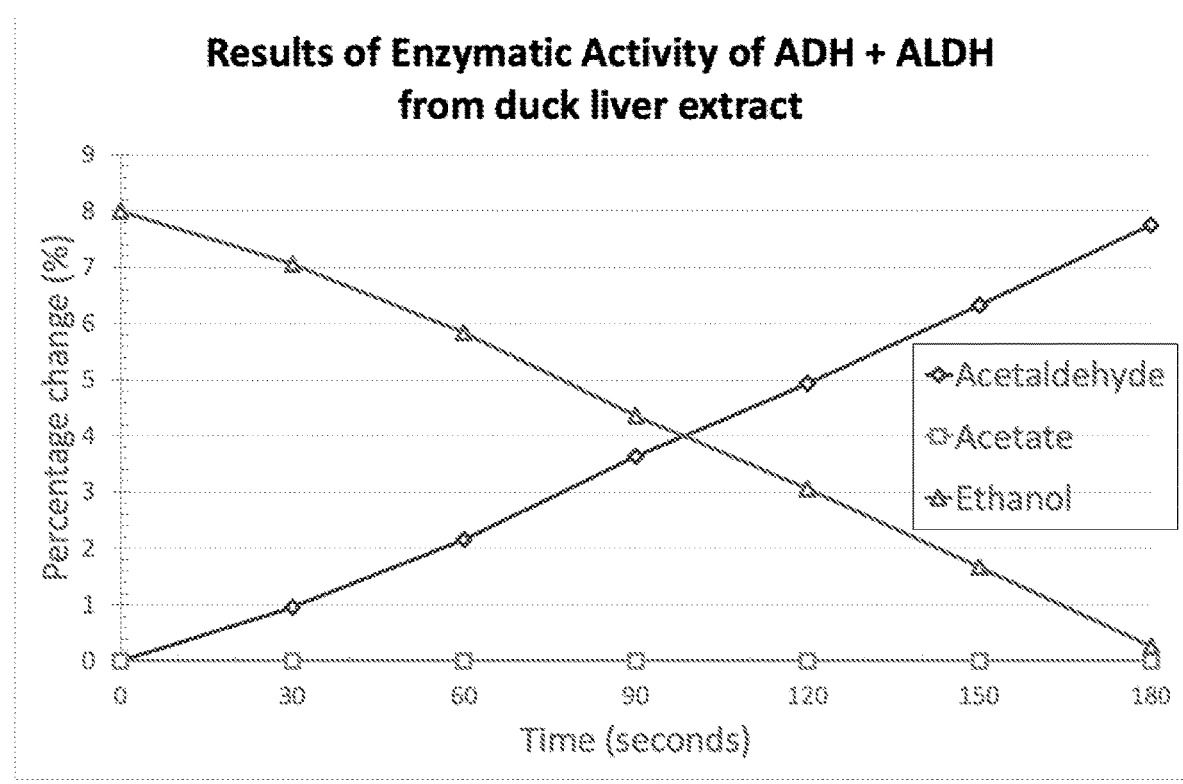
FIG. 8 shows the result of in vitro enzymatic activity from an extract of duck liver in terms of the change in concentration of alcohol and its by-products or metabolites over time showing no increase in acetate due to the liver not containing ALDH.

The duck liver is sourced from local markets in Hong Kong in fresh form. Duck liver was determined to have only ADH enzyme without ALDH enzyme. The in vitro enzymatic activity results from livers of ducks (from supernatant of crude extract of duck liver) for ADH is 1.32 Unit. As seen in FIG. 8, there is no increase in acetate due to the liver not containing ALDH.

Example 9—Goose (Anser)

The goose liver is sourced from Hungary in frozen form. The goose liver is foie gras and contains too much fat in the liver, as a result, in vitro test of ADH & ALDH enzymes cannot be done.

Table 1 summarizes the in vitro test results of the molar ratio of ADH:ALDH in each animal.

TABLE 1

| Animal | ADH | : | ALDH |
|---|---|---|---|
| Cows | 1 | : | 28 |
| Lamb | 1 | : | 39 |
| Sheep | 1 | : | 51 |
| Pig | 1 | : | 0 |
| Horse | 1 | : | 5 |
| Donkey | 1 | : | 19 |
| Chicken | 1 | : | 3 |
| Duck | 1 | : | 0 |
| Goose | 0 | : | 0 |

Ratio

The enzymes extracted from the livers of the nine animals were tested in vitro and only six of them including cows, lamb, sheep, horse, donkey and chicken were found to contain both ADH and ALDH. From the test results, the range of the molar ratio of ADH:ALDH among these six animals is from approximately 1:3 to approximately 1:51.

The in vitro enzymatic activity of liver extract from cows, lamb, sheep, horse, donkey and chicken are illustrated in Table 1, FIG. 2 to FIG. 7 respectively.

From the results, it can be concluded that the livers of herbivores contained both ADH and ALDH; for omnivores that eat both plant and animal matter, their livers contained only ADH but did not have ALDH.

In one aspect, the present invention produces a high-quality therapeutic enzyme remedy in an enteric capsule form to enhance degradation of alcohol in the human body, in order to relieve veisalgia and symptoms associated therewith for both casual and frequent alcohol drinkers. It is a freeze-dried powder from extract of bovine, ovine, equine or galline liver, or a mixture of extracts from different animals, by proprietary extraction and isolation methods that produce a product safe for human consumption and effective for alcohol degradation.

Using extraction and isolation methods, ADH and ALDH enzymes are successfully extracted from livers of different origin, including cow, lamb, sheep, horse, donkey or chicken. The extracts were freeze-dried and stored as dried powder.

From the in-house stability test of the freeze-dried powder from bovine and ovine liver extract, it shows very good stability when stored more than 12 months at room temperature and dry humidity.

Figure 10:
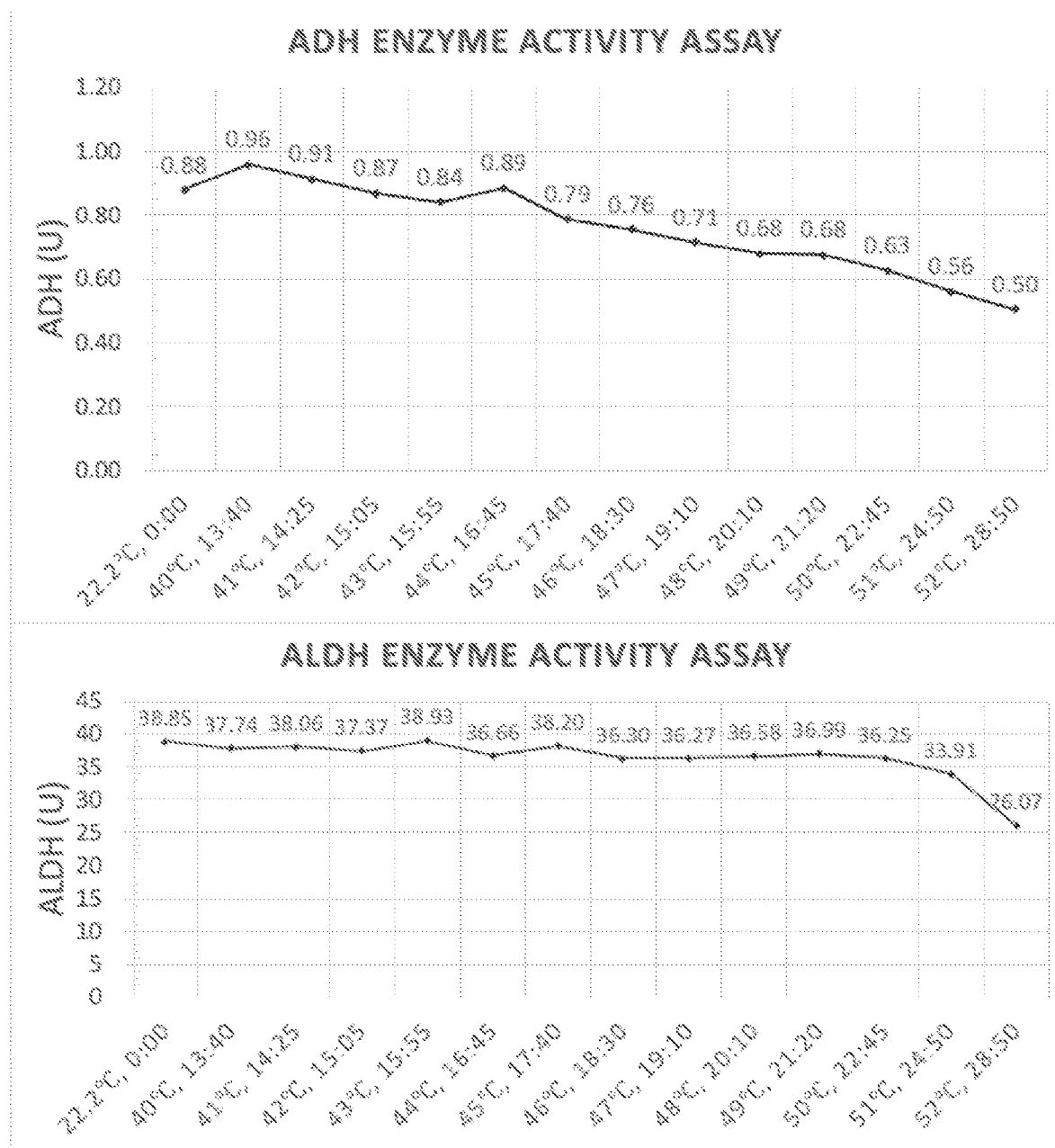
FIG. 10 shows the result of in vitro enzymatic activity of the contents of ADH and ALDH from cows' liver extract during heating of the extract.
Figure 11:
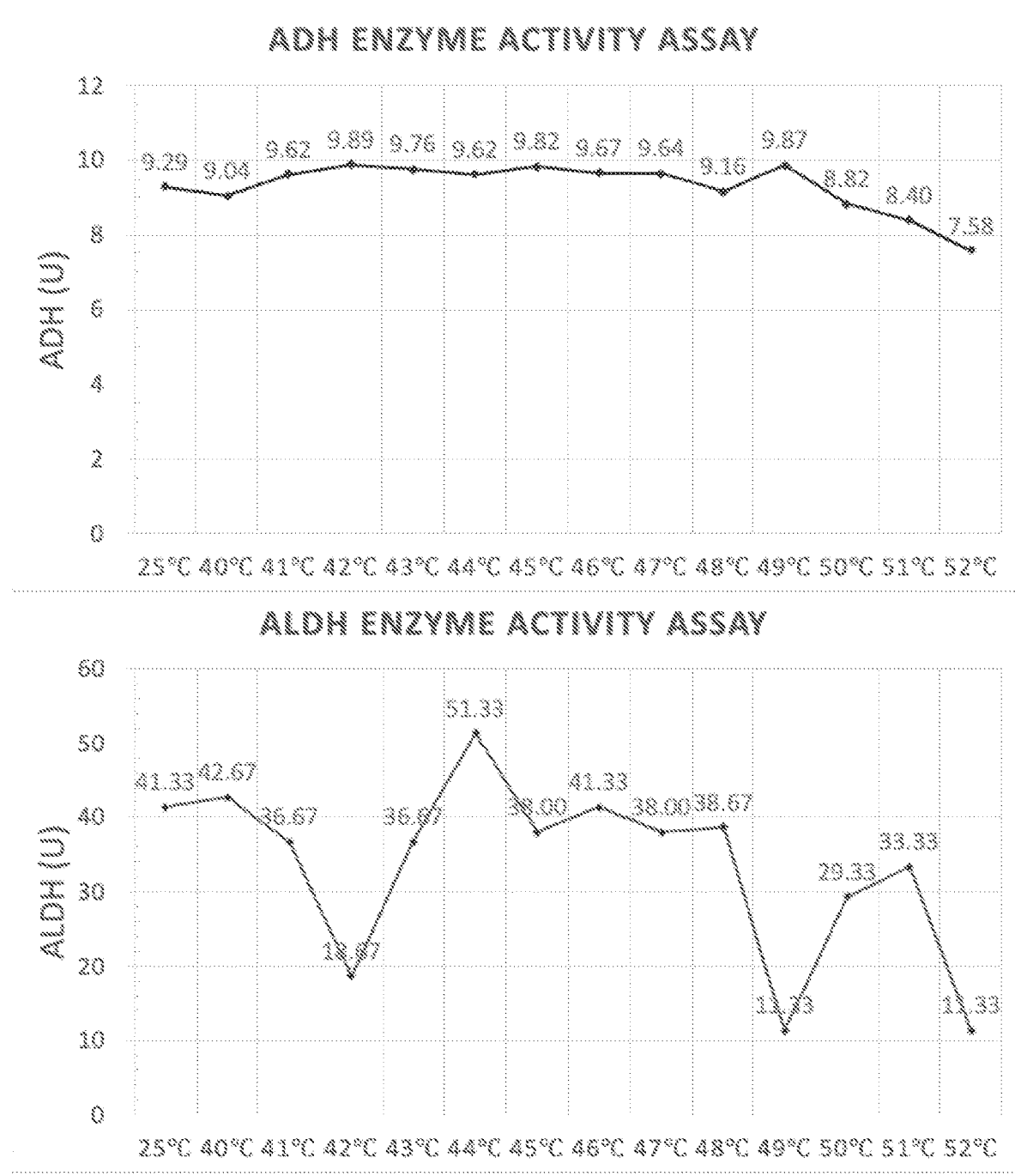
FIG. 11 shows the result of in vitro enzymatic activity of the contents of ADH and ALDH from horse liver extract during heating of the extract.
Figure 12:
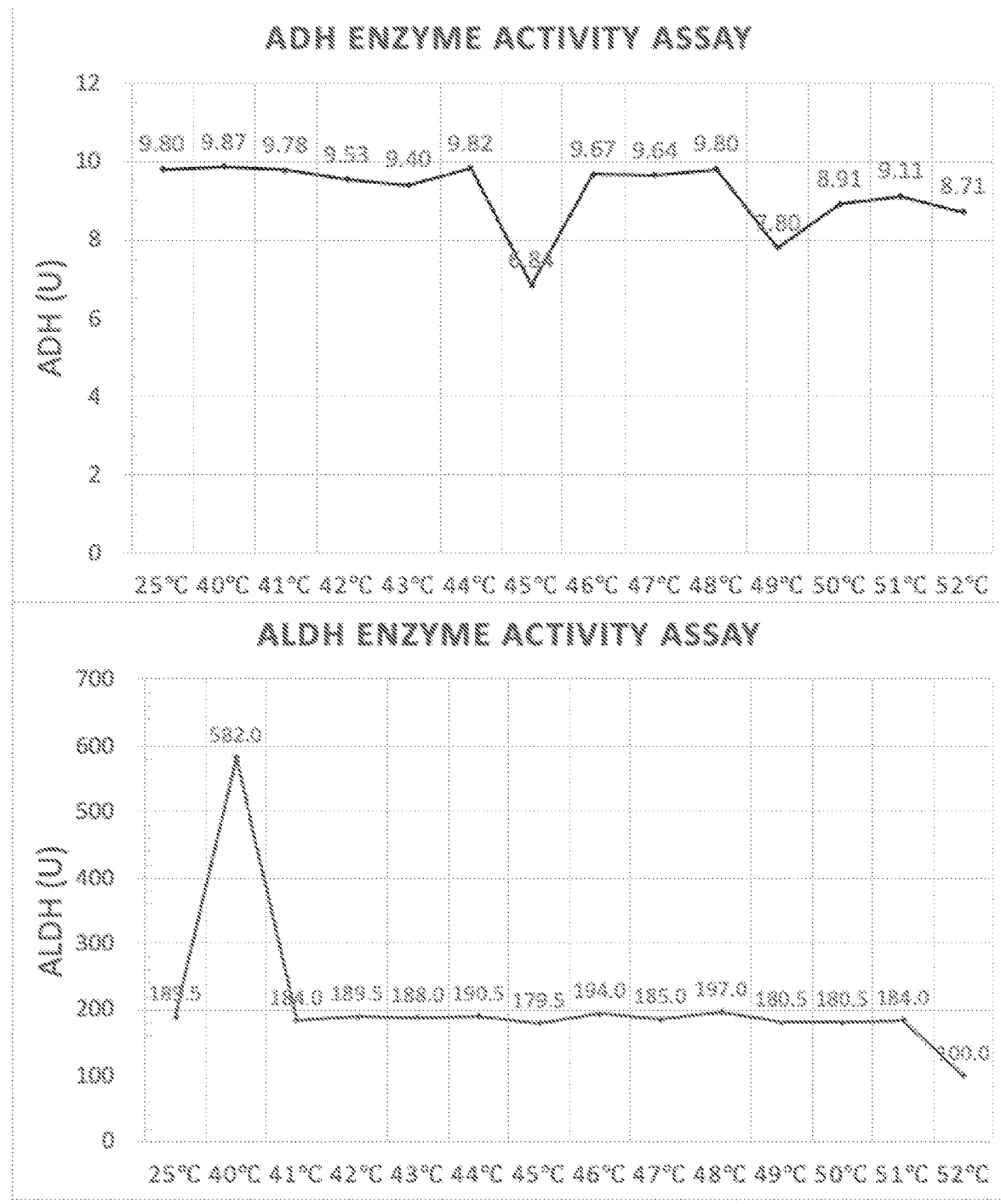
FIG. 12 shows the result of in vitro enzymatic activity of the contents of ADH and ALDH from donkey liver extract during heating of the extract.
Figure 13:
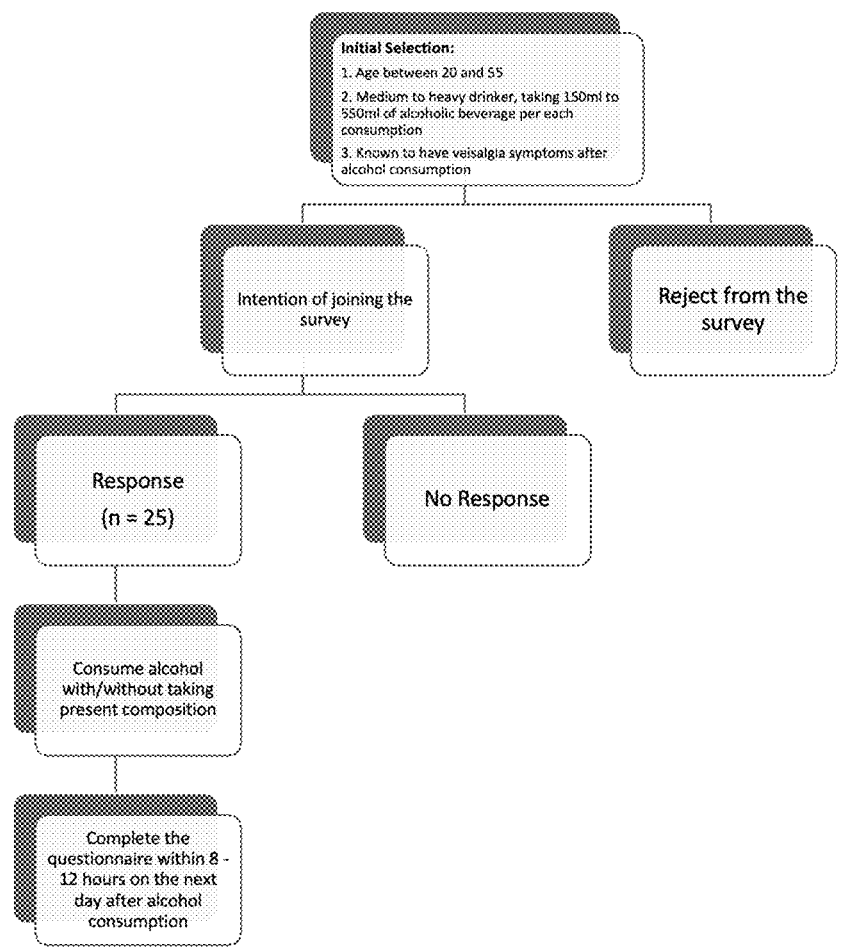
FIG. 13 shows the basic criteria of a survey to the effect of the present composition of this invention on the severity of veisalgia by using Alcohol Hangover Severity Scale (AHSS).

The present invention uses an inventive extraction method. The inventive extraction includes precise control of the heating and cooling of the extract from mammalian or ayes livers. It is found that when the extract from livers was heated to 40° C., an extract with the highest content of ADH, together with ADH and ALDH enzymes contents in the molar ratio range from approximately 1:3 to approximately 1:51, can be obtained. The in vitro enzymatic activity of contents of ADH and ALDH from the liver extract of cows, horse and donkey in this heating process are illustrated in FIG. 10 to FIG. 12.

Therefore, the therapeutic enzyme of the present invention could not be produced from the livers of pig, duck or goose. From an in vitro study of the present invention, ALDH was not present in the liver extract from pig, duck or goose, where ALDH is one of the main components in the present composition.

Optionally, the extracted enzymes may be packaged with antioxidants in enteric capsules. Antioxidants, along with other optional excipients, can protect the enzymes from degradation in order to maintain a longer shelf-life with maximum efficacy.

Oral supplements according to the present invention may be used in the following manner:

1. To enhance alcohol metabolism in the human body in order to relieve veisalgia and symptoms associated therewith.
2. To degrade alcohol to prevent Alcoholic Liver Disease ("ALD") and non-alcoholic fatty liver disease (NAFLD).

Two surveys were conducted by selecting subjects fulfilling the basic criteria shown in FIG. 11 to evaluate the effect of the present composition of this invention on the severity of veisalgia by using Alcohol Hangover Severity Scale (AHSS).

Survey 1—Test of freeze-dried powder from cows' liver extract (ADH:ALDH 1:28) encapsulated in enteric capsule:

Twenty-five subjects were successfully recruited and were asked to complete the same questionnaire twice during the 1-month test period. The subjects drank 150 ml to 550 ml of an alcoholic beverage with an alcohol content ranging from 15% to 55% along with food. The questionnaire was completed on the next day 8-12 hours after the alcohol consumption, where one questionnaire for each subject was completed under their normal alcohol intake practice, and the other was completed with taking the freeze-dried powder from cow's liver extract encapsulated in enteric capsule before alcohol consumption. Twelve symptoms including fatigue, apathy, concentration problems, clumsiness, confusion, thirst, sweating, shivering, stomach pain, nausea, dizziness and heart pounding were used to evaluate the severity of veisalgia for all subjects The subjects were asked to indicate to what extent they experienced the 12 symptoms mentioned above after they woke up. It can be seen that 2 subjects did not develop veisalgia and/or any symptoms associated therewith, no matter with or without taking the above mentioned composition during the test period; 22 subjects developed veisalgia and/or symptoms associated therewith, in the absence of the above mentioned composition, but veisalgia or the associated symptoms was/were relieved after taking the above mentioned composition; 1 subject developed veisalgia and the associated symptoms, whether or not the above mentioned composition was taken. From the AHSS survey, about 88% of the subjects had a positive response towards to the above-mentioned composition, with significant relief of their veisalgia and the associated symptoms after the alcohol consumption.

Survey 2—Test of freeze-dried powder from donkey liver extract (ADH:ALDH 1:19) encapsulated in enteric capsule:

Nine subjects were successfully recruited and were asked to complete the same questionnaire twice during the 1-month test period. The subjects drank 100 ml to 300 ml of alcoholic beverage with alcohol content ranging from 50% to 53% with food. The questionnaire was completed on the next day 8-12 hours after alcohol consumption, where one questionnaire for each subject was completed under their normal alcohol intake practice, and the other was completed after taking the freeze-dried powder from donkey liver extract encapsulated in enteric capsule before alcohol consumption. Twelve symptoms including fatigue, apathy, concentration problems, clumsiness, confusion, thirst, sweating, shivering, stomach pain, nausea, dizziness and heart pounding were used to evaluate the severity of veisalgia for all subjects The subjects were asked to indicate to what extent they experienced the 12 symptoms mentioned above after they woke up. It can be seen that 8 subjects developed veisalgia and/or symptoms associated therewith, in the absence of the above-mentioned composition, but veisalgia or the associated symptoms was/were relieved after taking the above-mentioned composition; 1 subject developed mild veisalgia and the associated symptoms, whether or not the above-mentioned composition was taken. From the AHSS survey, about 89% of the subjects had a positive response towards to the above-mentioned composition, with significant relief of their veisalgia and the associated symptoms after the alcohol consumption.

As determined from the plots in FIG. 2 to FIG. 7, the equilibrium mid-point of ethanol and acetate from the in vitro tests were determined. The equilibrium mid-points are listed in Table 2.

TABLE 2

| Animal | Ratio | | | Equilibrium mid point (seconds) |
|---|---|---|---|---|
| | ADH | : | ALDH | |
| Cows | 1 | : | 28 | 88 |
| Lamb | 1 | : | 39 | 100 |
| Sheep | 1 | : | 51 | 102 |
| Horse | 1 | : | 5 | 75 |
| Donkey | 1 | : | 19 | 73 |
| Chicken | 1 | : | 3 | 95 |

From the data in Table 2, it can be seen that even though the ratios of ADH:ALDH vary from 1:3 to 1:51 from the 6 animals (cows, lamb, sheep, horse, donkey and chicken), each ADH:ALDH ratio demonstrates a similar equilibrium mid-point for ethanol and acetate. That is, the in vitro experiments indicate that all ratios are effective on breaking down alcohol, and then acetaldehyde, into their respective metabolites, at approximately the same rate without the accumulation of the first metabolites. Further, the results of the two surveys set forth above show substantially similar reductions in veisalgia symptoms for ADH:ALDH of 1:19 and 1:28. Therefore, based on the similar equilibrium mid-points and the human survey results, it has been determined that the breakdown of metabolites is efficacious over the entire range from 1:3 to at least 1:51. Consequently, the different ratios of ADH:ALDH in the range from 1:3 to 1:51 in the composition will be efficacious in reducing veisalgia symptoms. Further, based on these same metabolic mechanisms, the compositions may be effective in reducing or preventing NAFLD.

At higher doses, the enzyme compositions of the present invention may be used as an oral or injectable medication which can rapidly remove alcohol in emergency situations of acute alcohol intoxication. The present composition can reduce and prevent the severity of acute alcohol intoxication by efficiently converting alcohol to non-harmful substances before body tissues and organs, for instance, liver, uptake harmful levels of alcohol from blood.

For injectable formulations and optionally for oral formulations, recombinant DNA technology by introducing mammalian expression vectors carrying genes of human h-ADH and h-ALDH into safe and well-studied mammalian cell lines may be employed. These mammalian-cells-expressed target enzymes are further isolated and purified by chromatographic techniques. The present invention is useful to produce clinical grade h-ADH and h-ALDH for effective intravenous ("I.V.") or intramuscular ("I.M.") infusion of therapeutic enzyme remedies for emergency use in hospitals and clinics.

The human genome includes 19 ALDH genes. ALDH1 is primarily found in the liver and may be used in the enzyme extract version of the present invention. Another ALDH is ALDH2 which is found in the mitochondria. ALDH2 may be selected as the ALDH used in the present invention; its sequence is represented by SEQ ID NO: 1:

```
MSAAATQAVP APNQQPEVFC NQIFINNEWH DAVSRKTFPT

VNPSTGEVIC QVAEGDKEDV DKAVKAARAA FQLGSPWRRM

DASHRGRLLN RLADLIERDR TYLAALETLD NGKPYVISYL

VDLDMVLKCL RYYAGWADKY HGKTIPIDGD FFSYTRHEPV

GVCGQIIPWN FPLLMQAWKL GPALATGNVV VMKVAEQTPL

TALYVANLIK EAGFPPGVVN IVPGFGPTAG AAIASHEDVD

KVAFTGSTEI GRVIQVAAGS SNLKRVTLEL GGKSPNIIMS

DADMDWAVEQ AHFALFFNQG QCCCAGSRTF VQEDIYDEFV

ERSVARAKSR VVGNPFDSKT EQGPQVDETQ FKKILGYINT

GKQEGAKLLC GGGIAADRGY FIQPTVFGDV QDGMTIAKEE

IFGPVMQILK FKTIEEVVGR ANNSTYGLAA AVFTKDLDKA

NYLSQALQAG TVWVNCYDVF GAQSPFGGYK MSGSGRELGE

YGLQAYTEVK TVTVKVPQKN S
```

Recombinant ALDH such as ALDH2 is commercially available from suppliers such as Sigma Aldrich. Examples of recombinant techniques to product ALD and ALDH are described in Nene et al., J. Biomed. Sci. 2017, 24: 3, published 5 Jan. 2017, the disclosure of which is incorporated by reference herein.

The active ingredients in the formulation of the present invention may be incorporated into an oral formulation that may be administered as a dietary supplement product. A potential health benefit of this product is to relieve veisalgia and the associated symptoms for casual and frequent alcohol drinkers. The product should be taken before consuming alcohol.

References:

The disclosures of each of the following references are incorporated by reference herein.
1. Thomas D. Hurley, Howard J. Edenberg, Ting-Kai Li. Pharmacogenomics of Alcoholism. In: Pharmacogenomics: The Search for Individualized Therapies, Germany Wiley-VCH, Weinheim, Chapter 21, p. 417-441.
2. Nene et al., J. Aldehyde dehydrogenase 2 activation and coevolution of its εPKC-mediated phosphorylation sites. Biomed. Sci. 2017, 24: 3.

What is claimed is:

1. A composition for converting ethanol to acetaldehyde and subsequently converting the acetaldehyde to acetate, said composition comprising alcohol dehydrogenase and aldehyde dehydrogenase from livers of cows, lamb, sheep, horse, donkey and chicken in a molar ratio 1:28, 1:39, 1:51, 1:5, 1:19 and 1:3 respectively where the enzyme composition is formulated as an oral or injectable medication to reduce or prevent the severity of acute alcohol intoxication.

2. The composition of claim 1, wherein the alcohol dehydrogenase and aldehyde dehydrogenase are sourced from the same or two different animal origins.

3. The composition of claim 2, wherein the alcohol dehydrogenase and aldehyde dehydrogenase are sourced from the same animal origin and the animal is selected from bovine, ovine, equine, anas or galline.

4. The composition of claim 2, wherein the alcohol dehydrogenase and aldehyde dehydrogenase are sourced from different animal origin, and the animal is selected from bovine, ovine, equine, galline, anas, or any combination thereof.

5. The composition of claim 2, wherein the alcohol dehydrogenase and aldehyde dehydrogenase are more abundant in livers than other body parts of the animal.

6. The composition of claim 1, wherein the composition is to be consumed orally by the subject before and/or after ethanol consumption.

7. The composition of claim 1, wherein the alcohol dehydrogenase and aldehyde dehydrogenase are in solid form.

8. The composition of claim 1, wherein the composition is a controlled-release system, and further comprises an enteric coating encapsulating the alcohol dehydrogenase and aldehyde dehydrogenase to form an enteric capsule, tablet and/or pill.

9. A method for lowering ethanol content and/or preventing accumulation of one of metabolites of the ethanol in a subject, the method comprising consuming the composition of claim 1 by the subject before and/or after consuming ethanol.

10. The method of claim 9, wherein the composition is orally consumed by the subject before and/or after ethanol consumption.

11. The method of claim 9, wherein the composition is formulated in an enteric capsule, tablet, and/or pill which enables a controlled-release system of delivering the alcohol dehydrogenase and aldehyde dehydrogenase to a target site of the subject.

12. The method of claim 11, wherein the alcohol dehydrogenase and aldehyde dehydrogenase are delivered to blood streams via gastrointestinal tract of the subject.

13. The method of claim 9, wherein the alcohol dehydrogenase and aldehyde dehydrogenase are in solid form.

* * * * *

SEQUENCE LISTING

<160> NUMBER OF SEQ ID NOS: 1

<210> SEQ ID NO 1
<211> LENGTH: 501
<212> TYPE: PRT
<213> ORGANISM: Homo sapiens

<400> SEQUENCE: 1

Met Ser Ala Ala Thr Gln Ala Val Pro Ala Pro Asn Gln Gln Pro
1               5                   10                  15

Glu Val Phe Cys Asn Gln Ile Phe Ile Asn Asn Glu Trp His Asp Ala
                20                  25                  30

Val Ser Arg Lys Thr Phe Pro Thr Val Asn Pro Ser Thr Gly Glu Val
            35                  40                  45

Ile Cys Gln Val Ala Glu Gly Asp Lys Glu Asp Val Asp Lys Ala Val
    50                  55                  60

Lys Ala Ala Arg Ala Ala Phe Gln Leu Gly Ser Pro Trp Arg Arg Met
65                  70                  75                  80

Asp Ala Ser His Arg Gly Arg Leu Leu Asn Arg Leu Ala Asp Leu Ile
                85                  90                  95

Glu Arg Asp Arg Thr Tyr Leu Ala Ala Leu Glu Thr Leu Asp Asn Gly
                100                 105                 110

Lys Pro Tyr Val Ile Ser Tyr Leu Val Asp Leu Asp Met Val Leu Lys
            115                 120                 125

Cys Leu Arg Tyr Tyr Ala Gly Trp Ala Asp Lys Tyr His Gly Lys Thr
    130                 135                 140

Ile Pro Ile Asp Gly Asp Phe Phe Ser Tyr Thr Arg His Glu Pro Val
145                 150                 155                 160

Gly Val Cys Gly Gln Ile Ile Pro Trp Asn Phe Pro Leu Leu Met Gln
                165                 170                 175

Ala Trp Lys Leu Gly Pro Ala Leu Ala Thr Gly Asn Val Val Val Met
                180                 185                 190

Lys Val Ala Glu Gln Thr Pro Leu Thr Ala Leu Tyr Val Ala Asn Leu
            195                 200                 205

Ile Lys Glu Ala Gly Phe Pro Pro Gly Val Val Asn Ile Val Pro Gly
    210                 215                 220

Phe Gly Pro Thr Ala Gly Ala Ala Ile Ala Ser His Glu Asp Val Asp
225                 230                 235                 240

Lys Val Ala Phe Thr Gly Ser Thr Glu Ile Gly Arg Val Ile Gln Val
                245                 250                 255

Ala Ala Gly Ser Ser Asn Leu Lys Arg Val Thr Leu Glu Leu Gly Gly
                260                 265                 270

Lys Ser Pro Asn Ile Ile Met Ser Asp Ala Asp Met Asp Trp Ala Val
            275                 280                 285

Glu Gln Ala His Phe Ala Leu Phe Phe Asn Gln Gly Gln Cys Cys Cys
    290                 295                 300

Ala Gly Ser Arg Thr Phe Val Gln Glu Asp Ile Tyr Asp Glu Phe Val
305                 310                 315                 320

Glu Arg Ser Val Ala Arg Ala Lys Ser Arg Val Val Gly Asn Pro Phe
                325                 330                 335

Asp Ser Lys Thr Glu Gln Gly Pro Gln Val Asp Glu Thr Gln Phe Lys
            340                 345                 350

Lys Ile Leu Gly Tyr Ile Asn Thr Gly Lys Gln Glu Gly Ala Lys Leu
    355                 360                 365

```
Leu Cys Gly Gly Gly Ile Ala Ala Asp Arg Gly Tyr Phe Ile Gln Pro
    370                 375                 380

Thr Val Phe Gly Asp Val Gln Asp Gly Met Thr Ile Ala Lys Glu Glu
385                 390                 395                 400

Ile Phe Gly Pro Val Met Gln Ile Leu Lys Phe Lys Thr Ile Glu Glu
                405                 410                 415

Val Val Gly Arg Ala Asn Asn Ser Thr Tyr Gly Leu Ala Ala Ala Val
            420                 425                 430

Phe Thr Lys Asp Leu Asp Lys Ala Asn Tyr Leu Ser Gln Ala Leu Gln
        435                 440                 445

Ala Gly Thr Val Trp Val Asn Cys Tyr Asp Val Phe Gly Ala Gln Ser
    450                 455                 460

Pro Phe Gly Gly Tyr Lys Met Ser Gly Ser Gly Arg Glu Leu Gly Glu
465                 470                 475                 480

Tyr Gly Leu Gln Ala Tyr Thr Glu Val Lys Thr Val Thr Val Lys Val
            485                 490                 495

Pro Gln Lys Asn Ser
            500
```